(12) United States Patent
Palin et al.

(10) Patent No.: US 9,753,044 B1
(45) Date of Patent: Sep. 5, 2017

(54) APPARATUS AND METHOD FOR DETECTING PARAMAGNETIC AND SUPERPARAMAGNETIC BIOMARKERS

(71) Applicants: William J. Palin, Cape Elizabeth, ME (US); Karen A. Palin, Cape Elizabeth, ME (US)

(72) Inventors: William J. Palin, Cape Elizabeth, ME (US); Karen A. Palin, Cape Elizabeth, ME (US)

(*) Notice: Subject to any disclaimer, the term of this patent is extended or adjusted under 35 U.S.C. 154(b) by 0 days.

(21) Appl. No.: 15/209,187

(22) Filed: Jul. 13, 2016

(51) Int. Cl.
*B01L 3/00* (2006.01)
*G01N 33/72* (2006.01)
*G01N 1/40* (2006.01)

(52) U.S. Cl.
CPC ............ *G01N 33/72* (2013.01); *G01N 1/40* (2013.01); *G01N 1/405* (2013.01); *G01N 2001/4038* (2013.01); *G01N 2333/445* (2013.01); *G01N 2800/26* (2013.01)

(58) Field of Classification Search
CPC ....... B01L 2400/043; B01L 2200/0647; B01L 3/502
USPC ................... 422/559, 547, 186.01
See application file for complete search history.

(56) References Cited

U.S. PATENT DOCUMENTS

| | | | |
|---|---|---|---|
| 6,672,458 | B2 | 1/2004 | Hansen et al. |
| 7,073,668 | B2 | 7/2006 | Alford et al. |
| 8,206,596 | B2 | 6/2012 | Wang et al. |
| 8,470,267 | B2 | 6/2013 | Holenstein et al. |
| 2004/0251211 | A1* | 12/2004 | Suddath ............ A23L 3/32 210/748.18 |
| 2007/0251885 | A1* | 11/2007 | Korpela ............ B03C 1/286 210/690 |
| 2012/0252088 | A1 | 10/2012 | Zhang et al. |

(Continued)

FOREIGN PATENT DOCUMENTS

| | | |
|---|---|---|
| EP | 2524730 | 11/2012 |
| GB | 2409829 | 7/2005 |

OTHER PUBLICATIONS

Afshar, R et al. Magnetic particle dosing and size separation in a microfluidic channel. Sensors and Actuators B 154: 73-80, 2011, 8 pages.

(Continued)

*Primary Examiner* — Natalia Levkovich
(74) *Attorney, Agent, or Firm* — Caseiro Burke LLC; Chris A. Caseiro

(57) ABSTRACT

An apparatus configured to enable the concentration of paramagnetic and/or superparamagnetic materials in a fluid for the purpose of examining such materials. The apparatus includes a magnet container arranged to be located proximate to a material container containing the materials to be examined. The magnet container includes therein a fluid and one or more magnets. The magnet container further includes means for controlling the movement of the one or more magnets in the fluid to allow the attraction of the paramagnetic and/or superparamagnetic materials in the material container to the one or more magnets as they travel in the magnet container so as to concentrate those materials. Several options for controlling the movement of the one or more magnets are described, including fluid viscosity selection, magnet shape and size selection, the use of an inclined pathway and the use of an inclined plane.

14 Claims, 6 Drawing Sheets

(56) References Cited

U.S. PATENT DOCUMENTS

2014/0080149 A1  3/2014  Goehde
2014/0251887 A1  9/2014  Siddiqi

OTHER PUBLICATIONS

Baglia, Mark L. Towards the use of monodisperse ferromagnetic particles in low resource malaria diagnostic devices. Diss. Vanderbilt University, 2016, 47 pages.

Keersten M. Davis, et el. Low-Resource Method for Extracting the Malarial Biomarker Histidine-Rich Protein II to Enhance Diagnostic Test Performance. Analytical Chemistry 84, 6136-6142, 2012, 7 pages.

Roderick M. Dirkzwager, et al. Development of Aptamer-Based Point-of-Care Diagnostic Devices for Malaria Using Three-Dimensional Printing Rapid Prototyping. ACSSensors 1 (4): 420-426, 2016, 7 pages.

Alan H Fairlamb, et al. A simple method for the purification of malarial pigment. Molecular and Biochemical Parasitology, 12: 307-3 12, 1984, 6 pages.

Stephan Karl, et al. A comparison of the sensitivities of detection of Plasmodium falciparum gametocytes by magnetic fractionation, thick blood film microscopy, and RT-PCR. Malaria Journal 8:98-105, 2009, 7 pages.

Surasak Kasetsirikul, et al. The development of malaria diagnostic techniques: a review of the approaches with focus on dielectrophoretic and magnetophoretic methods. Malaria Journal 15:358-371.2016, 14 pages.

Charles C Kim, et al. Improved methods for magnetic purification of malaria parasites and haemozoin. Malaria Journal 9: 17-21, 2010, 5 pages.

James J, Lai. Et al. Improving Lateral-Flow Immunoassay (LFIA) Diagnostics via Biomarker Enrichment for mHealth. In Avraham Rasooly and Keith E. Herold (eds.), Mobile Health Technologies: Methods and Protocols, Methods in Molecular Biology, vol. 1256, Springer Science+Business Media New York 2015, 13 pages.

Robert M. Nalbandian, et al. A molecular-based magnetic test for malaria. Clinical Microbiology and Infectious Disease 103: 57-64, 1995, 8 pages.

Michael A. Nash, et al. Multiplexed Enrichment and Detection of Malarial Biomarkers Using a Stimuli-Responsive Iron oxide and Gold Nanoparticle Reagent System. ACS Nano. 6(8): 6776-6785, 2012, 19 pages.

Alphonsus H C Ng et al. Digital Microfluidic Magnetic Separation for Particle-Based Immunoassays. Analytical chemistry 84: 8805-8812, 2012, 8 pages.

F Paul, et al. Separation of Malaria-infected Erythrocytes from Whole Blood: Use of a Selective High-Gradient Magnetic Separation Technique. Lancet, 2 (8237): 70-71, 1981, 2 pages.

Chayakom Phurimsak, et al. Phaseguide assisted liquid lamination for magnetic particle-based assays. Lab on a Chip 14: 2334-2343, 2014, 10 pages.

Dasem Ramadan, et al. Simultaneous magnetic particles washing and concentration in a microfluidic channel. Procedia Chemistry 1: 1499-1502, 2009, 6 pages.

Clotilde Ribaut, et al. Concentration and purification by magnetic separation of the erythrocytic stages of all human *Plasmodium* species. Malaria Journal 7:45-49, 2008, 5 pages.

Deborah Sumari, et al, Application of magnetic cytosmear for the estimation of Plasmodium falciparum gametocyte density and detection of asexual stages in asymptomatic children. Malaria Journal 15:113-121, 2016, 9 pages.

Peter A. Zimmerman, et al. Diagnosis of Malaria by Magnetic Deposition Microscopy. Am. J. Trop. Med. Hyg., 74(4): 568-572, 2006, 5 pages.

Peter A. Zimmerman, et al. Malaria diagnosis for malaria elimination. Current Opinion in Infectious Diseases 28:446-454, 2015, 9 pages.

Keersten M. Davis, et al. Low-Resource Method for Extracting the Malarial Biomarker Histidine-Rich Protein II to Enhance Diagnostic Test Performance, Supplemental Information, Vanderbilt University 2012, 17 pages.

Roderick M. Dirkzwager, et al. Development of Aptamer-Based Point-of-Care Diagnostic Devices for Malaria Using Three-Dimensional Printing Rapid Prototyping, Supplementary Information, University of Hong Kong, 7 pages.

Hali Bordelon, et al. Development of Low-Resource RNA Extraction Cassette Based on Surface Tension Valves, American Chemical Society: 2161-2168, 2011, 8 pages.

Stefan von Kann, et al. Nonmonotonic settling of a sphere in a cornstarch suspension. Physical Review E 84: 060401 (R), 2011, 8 pages.

Stefan von Kann, et al. Velocity oscillations and stop-go cycles: The trajectory of an object settling in a cornstarch suspension. Physical Review E 87: 042301, 2013, 14 pages.

\* cited by examiner

APPARATUS AND METHOD FOR DETECTING PARAMAGNETIC AND SUPERPARAMAGNETIC BIOMARKERS

BACKGROUND OF THE INVENTION

1. Field of the Invention

The present invention relates to apparatuses and methods for detecting hemozoin in a fluid. More particularly, the present invention relates to the detection of hemozoin in a fluid using a magnetic attraction element.

2. Description of the Prior Art

Current methods for detecting malaria in blood specimens are time consuming and costly, or lack clinical or analytical sensitivity and may not be environmentally friendly. A significant impediment to effective testing is the inability to obtain sufficient quantity of biomarker material early enough in the development of the disease to carry out effective treatment as soon as would be preferable. It is desirable to have an apparatus and related detection method that can be used to concentrate biomarker material effectively and in a timely manner. While the cost and timeliness of malaria testing is of significance, the present invention is not limited solely to the detection of that disease. Instead, the present invention is directed to the concentration of magnetic and paramagnetic biomarkers suitable for use in the detection of any condition of interest that requires the evaluation of magnetic and/or paramagnetic biomarkers.

As an aspect of the desired functionality of the present invention, it is noted that hemozoin is an attractive biomarker for malaria determination. Hemozoin is a paramagnetic material. As a result, it is attracted to a magnetic field. The present invention takes advantage of this characteristic to address the limitation of a lack of sufficient biomarker material to use in current malaria testing methods inexpensively and/or timely manner.

SUMMARY OF THE INVENTION

The present invention is an apparatus and related method that can be used to concentrate paramagnetic and/or superparamagnetic particles for the purpose of analyzing the collected particles as biomarkers. The apparatus includes one or more magnets that are positioned proximate to a container including a material to be evaluated. The material container may be a vial or a tube, for example. The material container includes a fluid to be analyzed, such as a blood specimen, for example, that includes paramagnetic and/or superparamagnetic material. The one or more magnets are positioned in relation to the material so as to enable the attraction thereto of the paramagnetic and/or superparamagnetic materials in the fluid. Such materials gather in the vicinity of the magnets and are thereby concentrated in the material container. A material of interest may be analyzed once the concentration thereof has reached a detectable level, which detectable level is a function of the material to be analyzed.

As noted, the apparatus of the present invention enables the concentration of magnetically susceptible particles contained in fluid in the material container. The one or more magnets are positioned with respect to the material container such that as the magnet moves, whether inside or outside of the container, any paramagnetic and/or superparamagnetic material contained in the fluid is attracted to the one or more magnets and thereby moves with the one or more magnets. The ability to concentrate desirable levels of material in the container for analysis purposes is dependent upon magnet strength, the size and magnetic attraction characteristics of the material under evaluation, the viscosity of the fluid containing the material, the proximity of the magnet to the material and the rate of movement of the magnet with respect to the fluid in the container. The apparatus of the present invention is established in multiple embodiments, each of which is configured to manage the movement of the magnet with respect to the fluid.

The present invention may be used to concentrate biomarker materials of interest that are themselves paramagnetic and/or superparamagnetic. In other words, the invention may be used directly with such materials. In addition, if there is an interest in concentrating materials without magnetic characteristics, the present invention may still be used to accomplish that goal. Specifically, the fluid containing a sample that includes a non-magnetic analyte of interest may be placed in the material container. Paramagnetic particles containing ligand-binding molecules are also inserted into the material container. The ligand-binding materials are selected for their ability to bind to the non-magnetic analyte of interest. As a result of that combination, a complex of paramagnetic material, binder and non-magnetic analyte of interest is formed. The material container including that complex is positioned adjacent to the magnet container as described herein and the one or more magnets are caused to be moved in a regulated manner so as to attract and concentrate the composition at an end of the material container. The material container alone or the combination of the material container and the magnet container can then be inverted, if needed, to position the complex near an opening of the material container for removal and insertion into an assay device. Alternatively, the complex may be evaluated without removing it from the material container.

The movement of the magnet may be regulated in two primary ways in the present invention. First, the one or more magnets may be placed in a separate magnet container, which magnet container is placed adjacent to the material container. The magnet container includes a fluid of selectable viscosity. The magnetic container is positioned so that the one or more magnets are allowed to descend by gravitational force from an upper section of the container to a lower section of the container. The viscosity of the fluid in the magnet container and the size and shape of the one or more magnets within that fluid dictate the rate of descent. As the one or more magnets descend, particles with magnetic characteristics in the material container that is adjacent to the magnet container move toward the inner perimeter of the material container and also descend at a rate substantially matching the descent of the one or more magnets in view of the magnetic attraction. The magnetically-susceptible particles are concentrated at the bottom of the material container when the one or more magnets reach the bottom of the magnet container, provided the magnets and the fluid containing the magnets are selected to establish a descent rate that enables enough particles in the material container to be attracted and concentrated for analysis purposes. The concentrated particles are then evaluated, either directly in the material container or they are moved to some type of test bed, including but not limited to, a microscope slide, an assay device, a separate vial or tube.

A second way of managing magnet movement in the apparatus of the present invention with respect to material in a material container also uses gravity to move the magnet down through the magnet container but regulates that movement with reduced dependency on the viscosity of the fluid within the magnet container. The fluid could be a gas such as air or it could be a liquid. One variant takes advantage of the Lenz Law, wherein a portion or all of the magnet container is made of Aluminum. Alternatively, the magnet container includes an Aluminum component to cause the magnet to slow. The other variant is the inclusion in the magnet container of a non-vertical incline that the magnet travels down. In that configuration, the magnet does not make a direct-line trip to the bottom of the magnet container. Instead, the incline extends the time period for the magnet to move from the top to the bottom of the magnet container, resulting in an overall slower velocity on that trip from top to bottom. Either of these two variants permit the use of a less viscous and less expensive fluid, e.g., water or a salt or sugar solution but not limited thereto. For the first such variant, the material container may be positioned adjacent to the magnet container. For the second such variant, the material container could also be positioned adjacent to the magnet container or the magnet container could be annular, with the material container positioned at the center of the annulus.

A third way of managing magnet movement in the apparatus of the present invention with respect to material in a material container also uses gravity to move the magnet down through the magnet container regulates that movement through movement of the entire magnet container. Specifically, one or more magnets are located within a fluid of selectable viscosity in the magnet container. The material container is placed on an incline. The magnet container is of a shape that permits it to roll down the incline. For example, the magnet container may be a round jar. The magnet container is positioned on top of the material container at its highest point on the incline and allowed to roll down the incline while on top of the material container. The angle of the incline, the viscosity of the fluid in the magnet container and the characteristics of the one or more magnets dictate the velocity of the magnet container moving down the incline. That velocity is therefore selectable and may be adjusted as needed to ensure that there is sufficient time to attract any paramagnetic and/or superparamagnetic particles in the material container to the magnet container to allow concentration of a desired amount of those particles at the lowest point of the material container positioned on the incline. The desired amount of particles to be attracted and concentrated is dependent on the evaluation to be conducted and the characteristics of the particles.

The combination of the one or more magnets and magnet movement regulation yields effective paramagnetic and/or superparamagnetic biomarker concentration. This combination may be used to concentrate for analysis hemozoin, for example, as part of a substantially less costly malaria test. It can also be used to concentrate other biomarker materials of interest.

DETAILED DESCRIPTION OF THE INVENTION

The present invention is an apparatus and related method for concentrating paramagnetic and/or superparamagnetic materials in a container for the purpose of evaluating those materials. The apparatus includes the combination of a magnet container and a materials container. The magnet container contains therein one or more magnets of selectable size and shape. The magnet container also includes a fluid of selectable viscosity that is arranged to aid in managing the rate of movement of the one or more magnets in the magnet container. The materials container includes a fluid within which an analyte of interest, such as a biomarker, for example, resides. The analyte has paramagnetic and/or superparamagnetic characteristics or is coupled to a material that has paramagnetic and/or superparamagnetic characteristics. The magnet container is positioned in proximity to the material container and configured to cause controlled movement of the one or more magnets. That controlled magnet movement causes corresponding movement of the analyte in the material container in a way that results in concentration of the analyte at an end of the material container, thereby enhancing the ability to evaluate the analyte.

Figure 1:
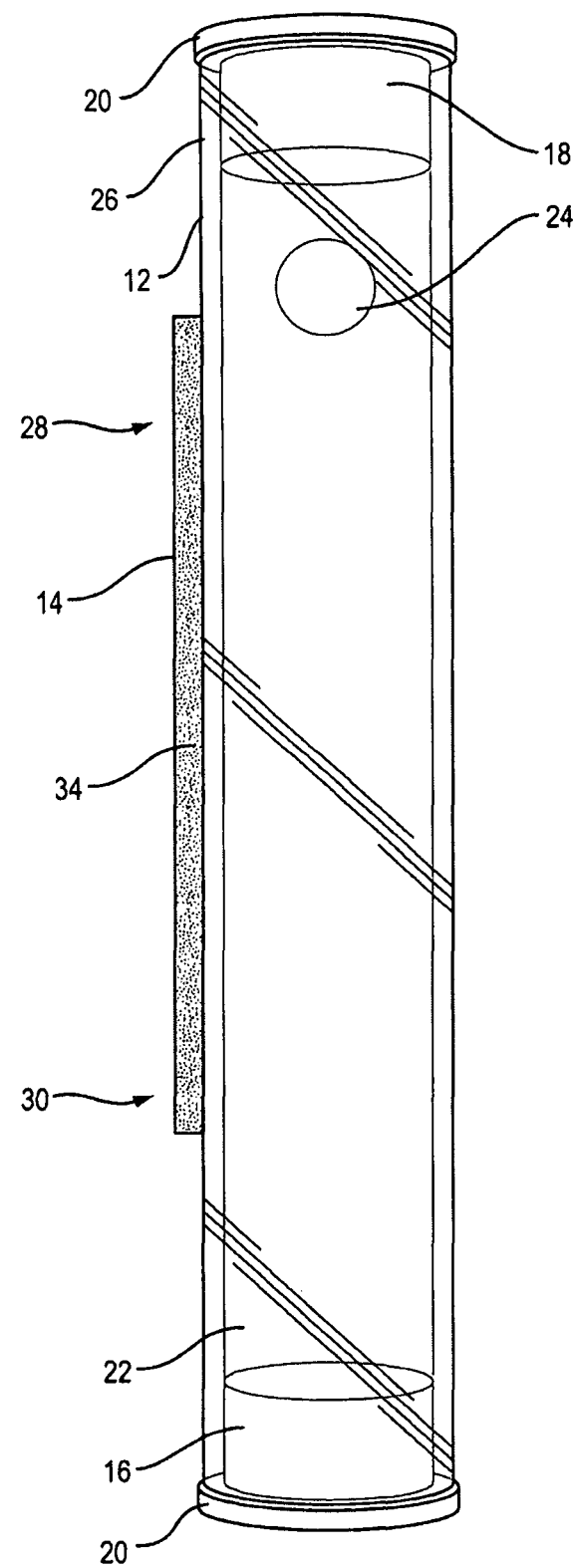
FIG. 1 is a side view of a first embodiment of the apparatus for detecting paramagnetic and/or superparamagnetic materials of the present invention.

A first embodiment of an apparatus 10 for concentrating an analyte is shown in FIG. 1. The apparatus 10 includes a magnet container 12 and a material container 14. The magnet container 12 includes a first end 16 and a second end 18. Either or both of the first end 16 and the second end 18 includes a removable cap 20. The cap 20 may be removed to allow delivery of a fluid 22 and a magnet 24 into an interior 26 of the magnet container 12. The fluid 22 is of selectable viscosity and type. For example, the fluid 22 may be corn syrup but is not limited thereto. The magnet 24 represents one or more magnets. The magnet 24 is of selectable size, shape and magnetic strength. For example, the magnet 24 may be spherical, discoidal or disk-shaped with concave or convex surfaces but is not limited thereto. Its exterior dimensions must be smaller than the interior dimensions of the magnet container 12 to ensure that the magnet 24 will move within the magnet container 12 such as when, for example, the magnet container 12 is first resting on the first end 16 and then rotated so that it is resting on the second end 18, causing the magnet 24 to move from the second end 18 to the first end 16 through the fluid 22. The selection of the fluid 22 and the magnet 24 determines the rate of movement of the magnet 24 from one end of the magnet container 12 to the other end.

The material container 14 includes a first end 28 and a second end 30. The material container 14 may be a vial or a tube, such as a capillary tube that may include caps at either or both of the first end 28 and the second end 30. As can be seen from FIG. 1, the material container 14 has a cross section that is significantly smaller than a cross section of the magnet container 12, and that the material container 14 is directly attached to the magnet container 12 along the length of the magnet container 12. It is to be understood that the cross section of the material container 14 is made at a right angle to the longitudinal axis of the material container 14 and that the cross section of the magnet container 12 is made at a right angle to the longitudinal axis of the magnet container 12. At least one of the caps may be removable to allow delivery of a fluid 34 therein. The fluid 34 may be aspirated into the material container 14 in a conventional manner. The fluid 34 is one under examination. Specifically, the fluid 34 includes at least one analyte to be analyzed. In particular, with respect to the present invention, the fluid 34 includes at last one material having a paramagnetic and/or superparamagnetic characteristic. The material container 14 is arranged for placement adjacent to the magnet container 12.

A desirable portion of the paramagnetic and/or superparamagnetic material in the fluid 34 is attracted to the magnet 24 in the magnetic container 12 given the proximity of the material container 14 to the magnet container 12. As the magnet 24 moves through the fluid 22 from one end to the other of the magnet container 12, the magnetically attracted materials in the material container 14 move with it. When the magnet 24 reaches the terminus of its travel in the magnet container 12, paramagnetic and/or superparamagnetic materials in the material container 14 have completed a similar travel condition. For example, if the material container 14 has been joined to the magnet container 12 such that the first end 16 of the magnet container 12 is aligned with the first end 28 of the material container 14 and the magnet 24 is located in the vicinity of the second end 18, then when the magnet container 12 and the material container 14 are rotated 180 degrees vertically, the magnet 24 moves from the second end 18 to the first end 16. At the same time, magnetically attracted material in the fluid 34 moves toward the magnet 24 and in a corresponding path in the material container 14 from the second end 30 the first end 28. The concentrated magnetically attracted material at the first end 28 may be examined therein or the material may be removed from the material container 14 for remote evaluation. The apparatus 10 provides an effective, efficient and inexpensive way to gather material for evaluation in a faster way than has been possible, particularly with respect to certain biomarkers of interest that otherwise must be slowly or expensively collected.

Figure 2:
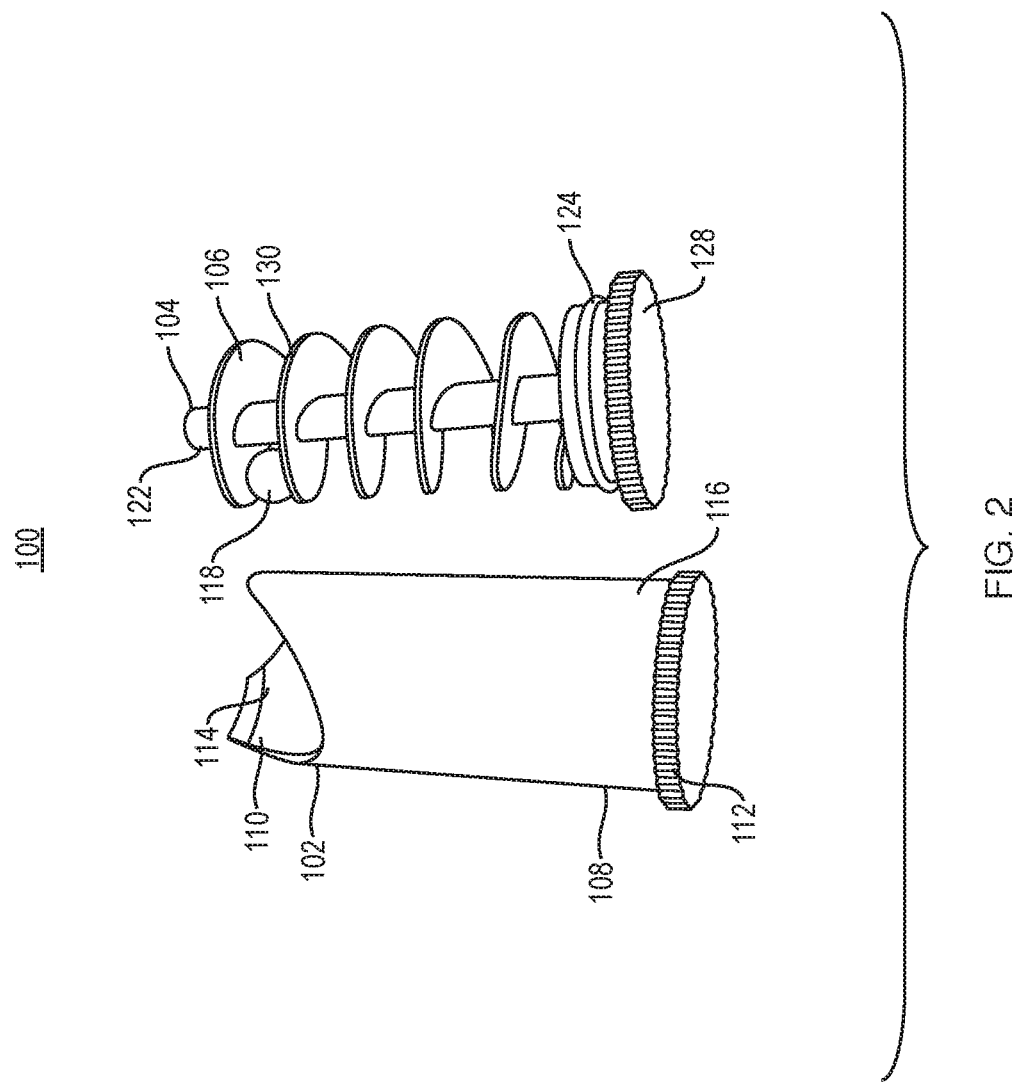
FIG. 2 is a side view of a second embodiment of the apparatus for detecting paramagnetic and/or superparamagnetic materials of the present invention.

A second embodiment of an apparatus 100 for concentrating an analyte is shown in FIG. 2. The apparatus 100 includes a magnet container 102, a material container 104 and an incline pathway 106. The magnet container 102 includes a first end 108 and a second end 110. The first end 108 includes a removable cap 112. The second end 110 has an opening 114 for insertion therein of the material container 104 and the incline pathway 106, as well as a fluid 116 and a magnet 118 into an interior 120 of the magnet container 102. The fluid 116 is of selectable viscosity and type. For example, the fluid 102 may be corn syrup or water but is not limited thereto. The magnet 118 represents one or more magnets. The magnet 118 is of selectable size and magnetic strength, and must be shaped to allow it to move down the incline pathway 106. For example, the magnet 118 may be a sphere or a discoid. Its exterior dimensions must be smaller than the interior dimensions of the magnet container 102 to ensure that the magnet 118 will move within the magnet container 102 such as when, for example, the magnet container 102 and the material container 104 are joined together and the combination is rotated.

The material container 104 includes a first end 122 and a second end 124. The first end 122 is threaded or otherwise configured to allow its removable insertion into opening 114 of the first end 108 of the magnet container 102. The second end 124 includes a cap 128 that is threaded or otherwise configured to enable its removable joining to the second end 110 of the magnet container 102. The magnet container 102 and the material container 104 are shown in FIG. 2 separated from one another, but when the first end 122 of the material container 104 is coupled to the port 126 of the magnet container 102 while the cap 128 is coupled to the second end 110, the apparatus 100 is a unitary structure with the material container 104 contained within the interior 120 of the magnet container 102. The opening 114 of the magnet container 102 does not extend completely through the cap 112 so that a fluid under examination in the material container 104 is retained therein when the magnet container 102 and the material container 104 are coupled together.

The incline pathway 106 is a helix-shaped structure sized to fit in the interior 120 of the magnet container 102 with its exterior dimensions small enough to fit within the magnet container 102 but large enough so that the magnet 118 can only travel on the incline pathway 106 as it traverses from one end of the magnet container 102 to the other without falling off the incline pathway 106. The incline pathway 106 is of an annular configuration with a portal 130 arranged to retain therein the material container 104. The incline pathway 106 may be separate from or joined to the material container 104. A fluid under examination may be aspirated into the material container 104 in a conventional manner. The fluid includes at least one analyte to be analyzed. In particular, with respect to the present invention, the fluid includes at last one material having a paramagnetic and/or superparamagnetic characteristic.

When the fluid under examination is in the material container 104 and the material container 104 is in the magnet container 102 and that combination is rotated 180 degrees, the magnet 118 moves down the incline pathway 106. Its rate of descent through the magnet container 102 is determined by its size and shape, as well as the angle of the include pathway 106 and the viscosity of the fluid 116, all of which are selectable to manage that rate of descent. As the magnet 118 moves on its controlled descent, a desirable portion of paramagnetic and/or superparamagnetic material in the fluid in the material container 104 is attracted to the magnet 118 moving downwardly with it. When the magnet 118 reaches the terminus of its travel in the magnet container 102, paramagnetic and/or superparamagnetic materials in the material container 104 have completed a similar descent to the second end 124 of the material container 104. The concentrated magnetically attracted material at the second end 124 may be examined therein or the material may be removed from the material container 104 for remote evaluation. The apparatus 100 provides an effective, efficient and inexpensive way to concentrate material for evaluation in a faster way than has been possible, particularly with respect to certain biomarkers of interest that otherwise must be slowly or expensively collected.

Figure 3:
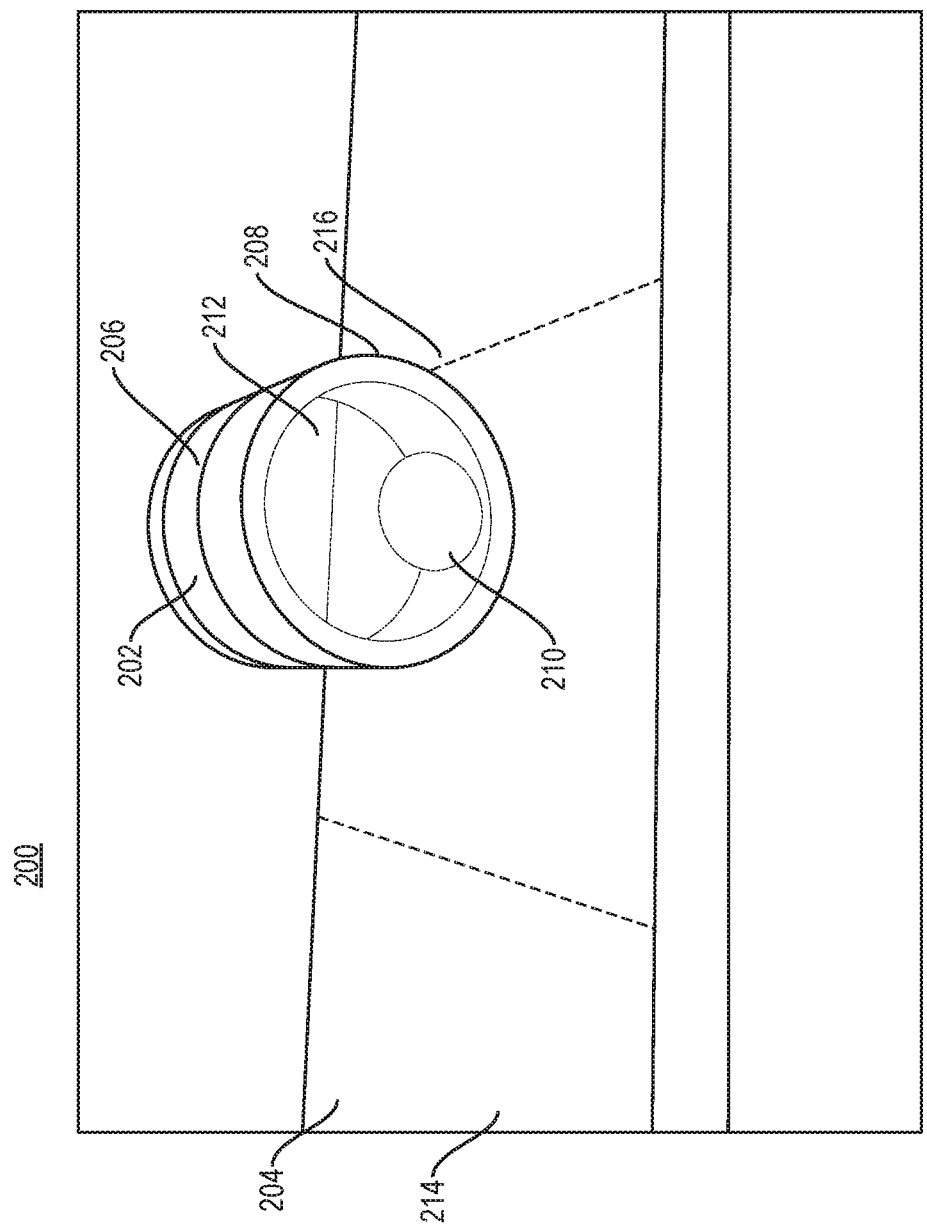
FIG. 3 is a bottom view of a third embodiment of the apparatus for detecting paramagnetic and/or superparamagnetic materials of the present invention positioned on an inclined plane substrate.

A third embodiment of an apparatus 200 for concentrating an analyte is shown in FIG. 3. The apparatus 200 includes a magnet container 202 and an incline plane 204. The magnet container 202 includes a housing 206, a cap 208, a magnet 210 and a fluid 212. The cap 208 is removably coupled to the housing 206, such as with threading of an exterior of the housing 206 and threading of an interior of the cap 208. The cap 208 may be removed from the housing 206 for insertion therein of the magnet 210 and the fluid 212. The fluid 212 is of selectable viscosity and type. For example, the fluid 212 may be corn syrup but is not limited thereto. The magnet 210 represents one or more magnets. The magnet 210 is of selectable size, shape and magnetic strength. For example, the magnet 210 may be disk-shaped or spherical. Its exterior dimensions must be smaller than the interior dimensions of the magnet container 202 to ensure that the magnet 210 will move within the magnet container 202 when the magnet container 202 moves. The selection of the fluid 212 and the magnet 210 determines the rate of movement of the magnet 210 down the incline plane 204. The housing 206 is preferably round or otherwise configured to enable its descent down the incline plane 204. The incline plane 204 may be any substrate having a first end 214 that is relatively higher than a second end 216 so that gravity may be used to effect the descent of the housing 206 from the first end 214 to the second end 216 when the magnet container 202 is placed on its side and positioned near the first end 214 of the incline plane 204. For example and without limitation, the substrate may be a form of container that retains therein the material container and that is configured to allow passage of the magnet container over it.

As has been noted, the viscosity of the fluid 212 and the configuration of the magnet 210 dictate the rate of descent of the magnet container 202 and, therefore, the rate of descent of the magnet 210. An analysis of three different magnets was conducted to determine the impact of those characteristics, if any, on the rate of descent of the magnet container 202 down the incline place 204. In all three examples, the fluid 212 in the housing 206 was corn syrup and the magnetic strength of the three example magnets was the same. A first magnet was disk-shaped with a ¼-inch diameter, a second magnet was disk-shaped with a ⅜-inch diameter, and a third magnet was disk-shaped with a ½-inch diameter. It was discovered that the ¼-inch and the ½-inch magnets traveled 7.5 centimeters down the incline plane having a 3.3-degree angle of descent at nearly identical times of about 26.5 seconds, while the ⅜-inch magnet took 263 seconds to complete the same course. That experiment confirmed that the rate of descent of the magnet container 202 and, therefore, the magnet 210 can be managed to a selectable effect dependent on fluid 212 and magnet 210 chosen.

Figure 4A:
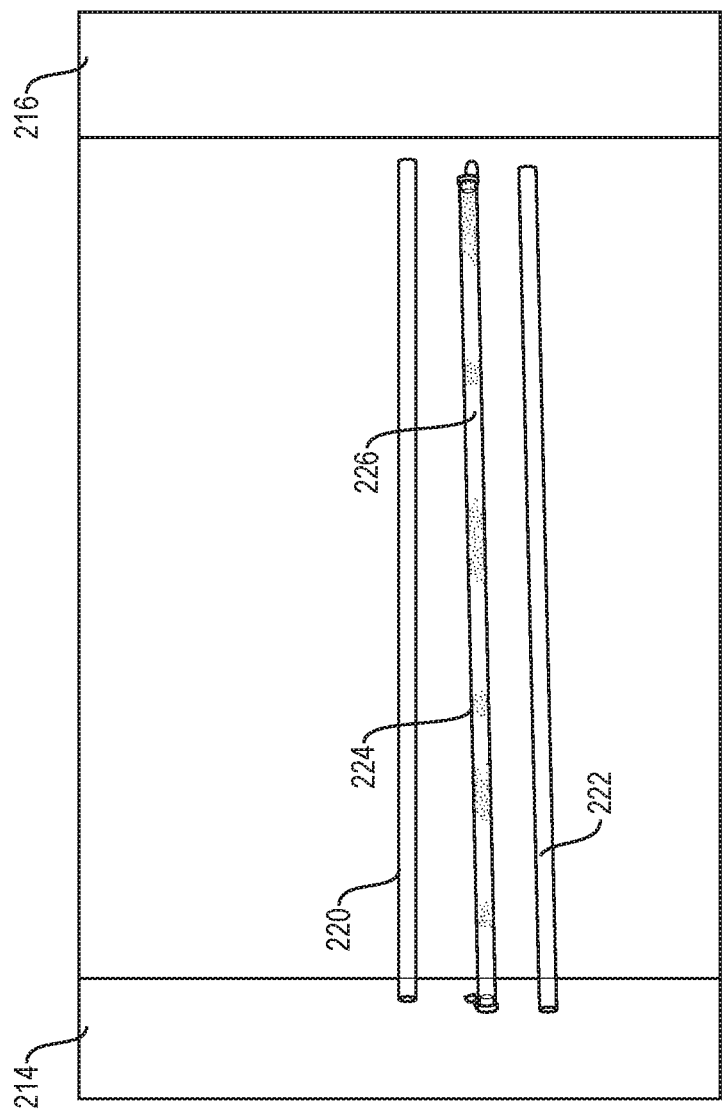
FIG. 4A is a top view of a set of capillary tubes including one in the center of the set that is a material container retaining a fluid with a paramagnetic material dispersed therein on the inclined plane substrate.
Figure 4B:
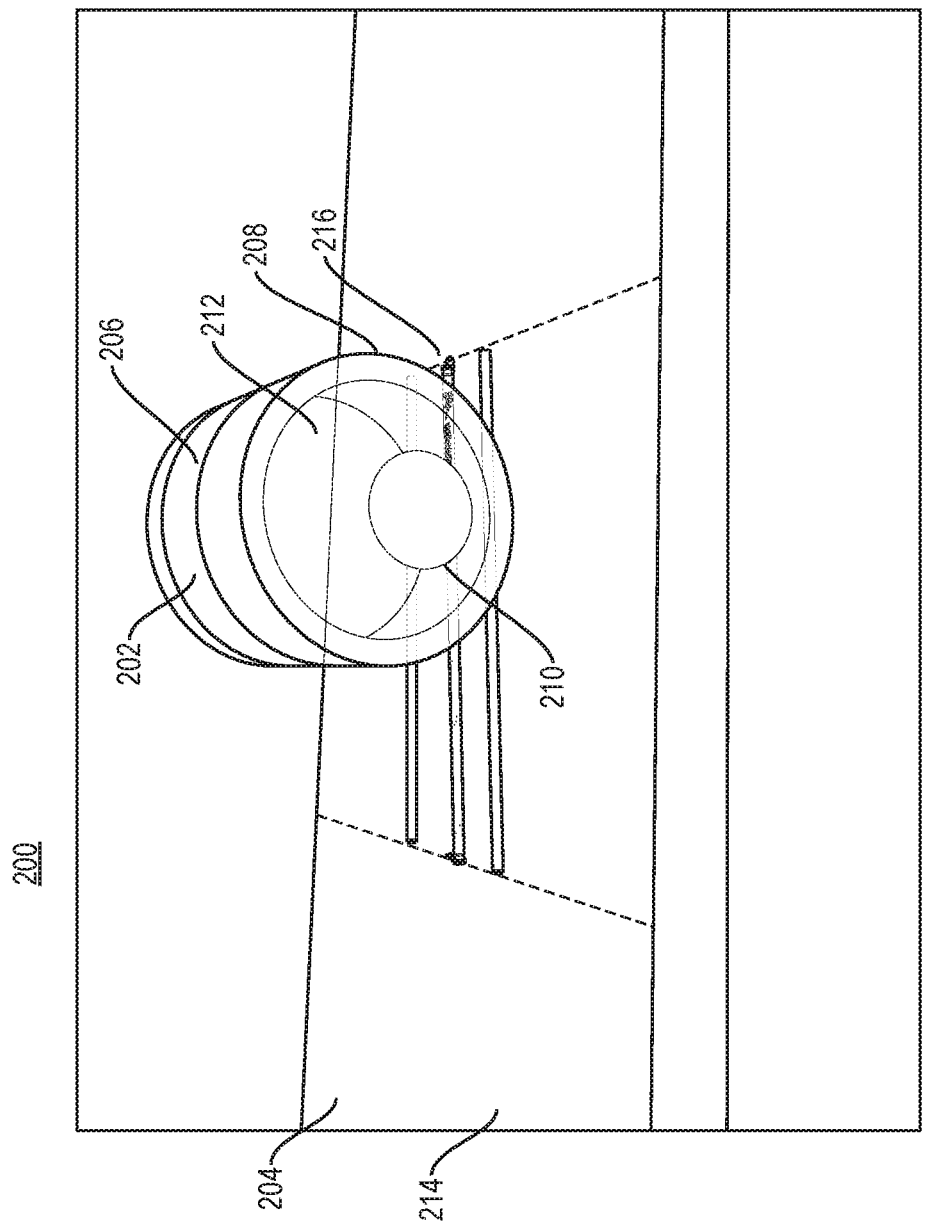
FIG. 4B is a top view showing the apparatus of FIG. 3 rolling on the capillary tubes of FIG. 4A.
Figure 5:
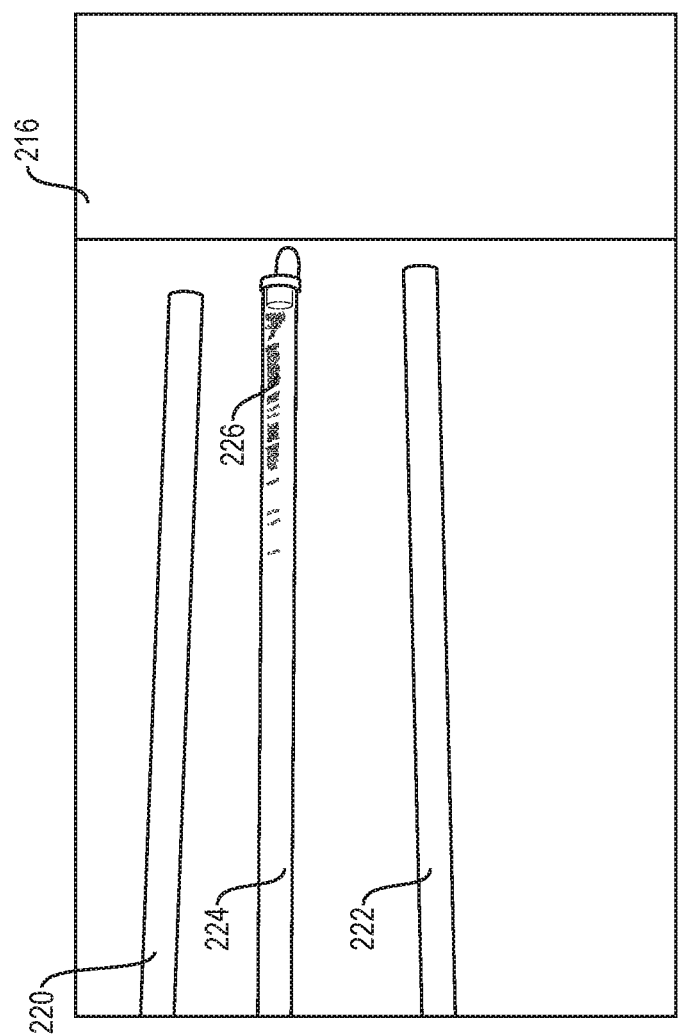
FIG. 5 is a top view of a portion of the set of capillary tubes of FIGS. 4A and 4B after the apparatus of FIG. 3 was rolled down the inclined plane over the set of capillary tubes showing the paramagnetic material concentrated at the lower end thereof.

The apparatus 200 can be used with a material container containing a fluid having an analyte of interest, wherein the analyte may be paramagnetic, superparamagnetic or linked to a paramagnetic and/or superparamagnetic binder. FIGS. 4A, 4B, and 5 show what can be accomplished using the apparatus 200. Three capillary tubes are shown in those drawings placed on the incline plane 204 extending from the first end 214 to the second end 216. Outer tubes 220 and 222 were empty while center tube 224 was filled with water containing one-micron paramagnetic particles 226 available from Polysciences, Inc. It can be seen in FIG. 4A that the paramagnetic particles 226 in tube 224 are widely dispersed throughout the tube 224. The magnet container 202 including the ⅜-inch magnet was placed on its side on top of the three capillary tubes at the first end 214 of the incline plane 204. The magnet container 202 was released and allowed to move over the three tubes as shown in FIG. 4B. It traveled in a stop-and-start fashion as the movement of the magnet 210 closest to the incline plane 204 lagged behind the movement of the housing 26. By the time the magnet container 202 reached the second end 216 of the incline plane 204, a substantial quantity of the paramagnetic particles 226 were concentrated at the second end 216 of the incline plane 204, as shown in FIG. 5. It can be seen from the results of this experiment that the apparatus 200 provides an effective, efficient and inexpensive way to concentrate material for evaluation in a more rapid manner than has been possible, particularly with respect to certain biomarkers of interest that otherwise must be slowly or expensively collected.

The present invention has been described with respect to various example embodiments. Nevertheless, it is to be understood that various modifications may be made without departing from the spirit and scope of the invention as described by the following claims.

What is claimed is:

1. An apparatus for concentrating paramagnetic and/or superparamagnetic materials in a sample fluid, the apparatus comprising:
   a magnet container having a length, a longitudinal axis, a first end and a second end, wherein the magnet container includes therein a fluid and one or more magnets, and
   a material container having a longitudinal axis, a first end and a second end, wherein the material container is a capillary tube having a cross section that is significantly smaller than a cross section of the magnet container, wherein the cross section of the material container is made at a right angle to the longitudinal axis of the material container and the cross section of the magnet container is made at a right angle to the longitudinal axis of the magnet container, wherein the material container is directly attached to the magnet container along the length of the magnet container, and wherein the material container includes therein the sample fluid, wherein the sample fluid includes one or more paramagnetic and/or superparamagnetic materials,
   wherein the fluid in the magnet container has a viscosity and the one or more magnets each has a size and a shape, wherein the viscosity of the fluid in the magnet container and the size and shape of the one or more magnets are configured to regulate a rate of descent by gravitational force of the one or more magnets in the fluid in the magnet container from either the first end to the second end of the magnet container or from the second end to the first end of the magnet container when the magnet container and the material container are oriented in a non-horizontal position at a rate that results in attraction of the paramagnetic and/or superparamagnetic materials in the material container toward the one or more magnets as the one or more magnets move down through the fluid in the magnet container such that at least a portion of the paramagnetic and/or superparamagnetic materials moves in the sample fluid in the material container in a direction and at a rate of descent that substantially matches the direction and rate of descent of the one or more magnets in the fluid in the magnet container to thereby concentrate the at least a portion of the paramagnetic and/or superparamagnetic materials in the sample fluid in the material container.

2. The apparatus of claim 1 wherein the at least a portion of the magnet container is made of Aluminum.

3. The apparatus of claim 1 wherein the sample fluid in the material container includes:
   a biomarker that is a nonmagnetic biomarker, and
   a binder,
   wherein the binder binds the nonmagnetic biomarker to the one or more paramagnetic and/or superparamagnetic materials in the sample fluid.

4. The apparatus of claim 1 wherein the fluid in the magnet container is corn syrup.

5. An apparatus for concentrating paramagnetic and/or superparamagnetic materials in a sample fluid, the apparatus comprising:
- a magnet container having a first end and a second end, wherein the magnet container includes therein a fluid, one or more magnets and a helix-shaped incline, wherein the helix-shaped incline has an annular configuration and a central through-hole, and
- a material container having a first end and a second end, wherein the material container is retained in the central through-hole of the helix-shaped incline of the magnet container so that the first end of the material container is aligned to the first end of the magnet container and the second end of the material container is aligned to the second end of the magnet container, and wherein the material container includes therein the sample fluid, wherein the sample fluid includes one or more paramagnetic and/or superparamagnetic materials,
- wherein the one or more magnets are positioned on the helix-shaped incline, which is configured to regulate a rate of descent by gravitational force of the one or more magnets in the fluid in the magnet container from the first end to the second end of the magnet container when the magnet container is oriented in a non-horizontal position at a rate that results in attraction of the paramagnetic and/or superparamagnetic materials in the sample fluid in the material container located in the central through-hole of the helix-shaped incline toward the one or more magnets as the one or more magnets move down the helix-shaped incline in the magnet container such that at least a portion of the paramagnetic and/or superparamagnetic materials moves in the material container in a direction and at a rate of descent that substantially matches the direction and rate of descent of the one or more magnets in the magnet container to thereby concentrate the at least a portion of the paramagnetic and/or superparamagnetic materials in the sample fluid in the material container.

6. The apparatus of claim 5 wherein the sample fluid in the material container includes:
- a biomarker that is a nonmagnetic biomarker, and
- a binder,
- wherein the binder binds the nonmagnetic biomarker to the one or more paramagnetic and/or superparamagnetic materials in the sample fluid.

7. The apparatus of claim 5 wherein the fluid in the magnet container is water and the one or more magnets are of a spherical shape.

8. The apparatus of claim 5 wherein the material container is a tube.

9. An apparatus for concentrating paramagnetic and/or superparamagnetic materials in a sample fluid, the apparatus comprising:
- a cylindrical magnet container, wherein the magnet container includes therein a fluid and one or more magnets, wherein the fluid has a viscosity and the one or more magnets each has a size and a shape,
- an inclined plane having a first end and a second end, wherein the first end of the inclined plane is higher than the second end of the inclined plane,
- a material container having a first end and a second end, wherein the material container is positioned on the inclined plane so that the first end of the material container is aligned to the first end of the inclined plane and the second end of the material container is aligned to the second end of the inclined plane, and wherein the material container includes therein the sample fluid, wherein the sample fluid includes one or more paramagnetic and/or superparamagnetic materials, and
- means to maintain the magnet container on the material container when the cylindrical magnet container moves over the material container,
- wherein when the magnet container is placed on the material container, oriented to roll down from the first end to the second end of the inclined plane, and rolls down the inclined plane, the viscosity of the fluid and the size and shape of the one or more magnets are configured to regulate a rate of descent down the inclined plane by gravitational force of the one or more magnets in the fluid in the magnet container at a rate that results in attraction of the paramagnetic and/or superparamagnetic materials in the material container toward the one or more magnets as the magnet container moves down the inclined plane such that at least a portion of the paramagnetic and/or superparamagnetic materials moves in the sample fluid in the material container in a direction and at a rate of descent that substantially matches the direction and rate of descent of the magnet container to thereby concentrate the at least a portion of the paramagnetic and/or superparamagnetic materials in the sample fluid in the material container.

10. The apparatus of claim 9 wherein the fluid in the magnet container is corn syrup and the one or more magnets are of a spherical shape.

11. The apparatus of claim 10 wherein the one or more magnets each has a ⅜-inch diameter.

12. The apparatus of claim 9 wherein the paramagnetic material and/or superparamagnetic material is a biomarker.

13. The apparatus of claim 9 wherein the sample fluid in the material container contains therein:
- a biomarker that is a nonmagnetic biomarker, and
- a binder,
- wherein the binder binds the nonmagnetic biomarker to the one or more paramagnetic and/or superparamagnetic materials in the sample fluid.

14. The apparatus of claim 1 wherein the magnet container is transparent or translucent.

* * * * *